(12) United States Patent
Brown

(10) Patent No.: US 11,707,558 B2
(45) Date of Patent: Jul. 25, 2023

(54) PHYSIOLOGICAL SIMULATOR INTEGRAL OF SHIELD FOR BREAST PUMP

(71) Applicant: Craig E Brown, Shelbyville, IL (US)

(72) Inventor: Craig E Brown, Shelbyville, IL (US)

(73) Assignee: Truvents, LLC, Shelbyville, IL (US)

( * ) Notice: Subject to any disclaimer, the term of this patent is extended or adjusted under 35 U.S.C. 154(b) by 292 days.

(21) Appl. No.: 16/873,237

(22) Filed: Mar. 2, 2020

(65) Prior Publication Data
US 2020/0206399 A1  Jul. 2, 2020

Related U.S. Application Data

(63) Continuation-in-part of application No. 29/651,629, filed on Nov. 6, 2018, now Pat. No. Des. 882,062.

(51) Int. Cl.
*A61M 1/06*  (2006.01)
*A61J 13/00* (2006.01)
*A61M 1/00*  (2006.01)

(52) U.S. Cl.
CPC .............. *A61M 1/066* (2014.02); *A61J 13/00* (2013.01); *A61M 1/06* (2013.01); *A61M 1/0697* (2021.05); *A61M 1/06935* (2021.05); *A61M 1/75* (2021.05); *A61M 1/82* (2021.05); *A61M 1/062* (2014.02); *A61M 1/069* (2021.05)

(58) Field of Classification Search
CPC ...... A61M 1/06; A61M 1/066; A61M 1/0697; A61M 1/069; A61M 1/06935; A61M 1/75; A61M 1/82; A61M 1/064; A61M 1/062; A61J 13/00
See application file for complete search history.

(56) References Cited

U.S. PATENT DOCUMENTS

| | | | |
|---|---|---|---|
| 4,468,552 A | 8/1984 | Morley | D24/109 |
| 4,772,262 A * | 9/1988 | Grant | A61M 1/06935 604/74 |
| 5,049,126 A | 9/1991 | Larsson | A61M 1/066 604/74 |
| 5,100,406 A * | 3/1992 | Panchula | A61M 1/066 604/74 |
| 5,885,246 A * | 3/1999 | Ford | A61M 1/066 604/74 |
| D456,897 S | 5/2002 | Atkin | D24/109 |
| 6,461,324 B1 * | 10/2002 | Schlensog | A61M 1/81 604/74 |
| 6,579,258 B1 | 6/2003 | Atkin | A61M 1/066 604/74 |
| D683,442 S | 5/2013 | Cudworth | D24/109 |
| 9,265,869 B2 | 2/2016 | Darnell | A61M 1/06 |
| 2003/0153869 A1 | 8/2003 | Ytteborg | A61M 1/064 604/74 |

(Continued)

*Primary Examiner* — Bhisma Mehta
*Assistant Examiner* — Robert F Allen

(57) ABSTRACT

The combination of a breast pump shield, with its ring, applied to the flange lower end of the shield, and the ring being C shaped in cross-section, having an upper flange, a lower flange, both integrally structured with a base wall. The physiological stimulator integrally formed with the lower flange of the sealing ring extends inwardly and upwardly within the shield, and therein functions as a means to place pressure upon the breast of the mother to help induce and stimulate the flow of breast milk during usage of the associated breast pump.

5 Claims, 4 Drawing Sheets

(56) References Cited

U.S. PATENT DOCUMENTS

| | | | |
|---|---|---|---|
| 2005/0154348 A1 | 7/2005 | Lantz | A61M 1/06 604/74 |
| 2005/0159701 A1 | 7/2005 | Conaway | A61M 1/06 604/74 |
| 2005/0251089 A1* | 11/2005 | Lee | A61M 1/06 604/74 |
| 2008/0208115 A1* | 8/2008 | Kliegman | A61M 1/066 604/74 |
| 2008/0243061 A1 | 10/2008 | Britto | A61M 1/06 604/74 |
| 2014/0323962 A1 | 10/2014 | Kooijker | A61M 1/06 604/74 |
| 2015/0314053 A1* | 11/2015 | Furrer | A61M 1/066 604/74 |
| 2016/0015876 A1 | 1/2016 | Tattersfield | A61M 1/064 604/74 |
| 2016/0256618 A1* | 9/2016 | Embleton | A61M 1/066 |
| 2018/0078687 A1* | 3/2018 | Alvarez | A61M 1/06935 |
| 2019/0175801 A1* | 6/2019 | Levine | A61M 1/062 |

* cited by examiner

PHYSIOLOGICAL SIMULATOR INTEGRAL OF SHIELD FOR BREAST PUMP

CROSS REFERENCE TO RELATED APPLICATIONS

This application is a continuation-in-part of the design patent application having Ser. No. 29/651,629, filed on Nov. 6, 2018.

FIELD OF INVENTION

This invention relates to an accessory for use with a breast pump, and more specifically to a physiological stimulator integral of the shield component for use with a breast pump, as when collecting breast milk or liquid from the mother, and incorporating means for physiologically functioning in the manner of the feeding infant when inducing the flow of such milk from the breast of the mother.

BACKGROUND OF THE INVENTION

As has been known forever, the breastfeeding of babies has been occurring as a natural way to give nutrition to the infant, during early childhood beginning years. With the advent of the economic revolution, where everyone in the family is now working, including the new mother, other means have been developed for the collection of breast milk, for eventual feeding to the infant, to achieve the benefits and enhanced results obtained through breastfeeding. For example, as is well known, and as studies have proven, feeding breast milk to an infant can add to its resistance against disease, and apparently has psychological advantages and benefits for the child, that are manifested in later years of life. Hence, the breast pump has been developed, as a means for collecting mother's milk, and for use for these purposes. Usually, breast pumps operate using a very high vacuum, or negative pressure, for withdrawing milk from the breast. These have been available for some time. Thus, before the new mother goes back to work, and while working, and many of them now do, they can non-physiologically withdraw some quantities of milk, for feeding to the infant during the day, as needed.

The concept of this invention is to provide a structure to a pump shield, that is used in proximity with the particular breast, and in combination with its sealing ring, can be applied to the breast pump, and provide for the enhanced withdraw of the breast milk for further usage. In essence, there is applied a structural member to the sealing ring used in conjunction with the pump shield, and which simulates the application of the infant's tongue, to the breast, to increase the flow of breast milk, during usage of the breast pump device.

SUMMARY OF THE INVENTION

This invention relates generally to improvements in the accessories used in conjunction with the breast pump, and more specifically utilizes a physiological stimulator that is applied in association with the breast shield, and its sealing ring, to function as an inducement to the enhanced flow of breast milk during operations of the associated pump. More particularly, the sealing ring that is used in combination with the shield, which together are applied to the target breast, has what is identified as a physiological stimulator, which is shaped similar to and located within the shield, to simulate the application of the infant's tongue, as when it naturally breastfeeds, for milk, during a feeding cycle. Importantly, the stimulator assumes the shape and actual peristaltic motion of the tongue during feeding. When negative pressure is applied from the pump, the stimulator provides the peristaltic action of the tongue to move milk from the proximal to the distal aspect of the breast. This is accomplished by the negative pressure of the pump applying more pressure proximally and automatically adjusting the pressure to move distally. This is done for the first time. Notably, it is also accomplished with no extra parts (it simply comes attached to the sealing ring). It may be optionally added later, if desired, to change the size of the stimulator, or add any number of stimulators, at any time. Also, there are no moving or complicated parts to break or replace. The sealing ring is shaped, and cross-sectioned, as an internally arranged C-ring, and into which the bottom flange of the pump shield locates, in preparation for its application. But, the C-ring, in cross-section, has an upper circular flange, a lower circular flange, and a base member that integrally connects all of these flange components together. Also, the sealing ring is preferably made from a soft material, to maximize sealing, allow for maximum comfort, and minimize the loss of any of the milk, which is critical, due to the frequent difficulty in obtaining sufficient amounts. Then, structurally extending inwardly and upwardly, for a specified distance, is the physiological stimulator that is integrally formed with the lower flange of the sealing ring, and which extends into the shield, proximate its interior surface, and thereat simulates the application of the infant's tongue, as during a natural feeding cycle, in order to induce a greater flow of breast milk from the lactating mother, when extracting an enhanced flow of breast milk for collection, for a later feeding of the nursing infant. The stimulator extends inwardly of the shield, and up approximately some distance within the shield, generally resting against the interior of the shield, to thereby act as a stimulating force against the surface of the breast, in order to enhance and induce the further flow of milk, from the mother.

As is further known, the invention includes this breast shield, that is applied to the breast of the new mother, and which may have various strappings for holding the breast shield in place, when used in conjunction with the pump, during its application. Obviously, when the shield is held in place, through the use of the latching straps, it places the physiological stimulator of the sealing ring, against the surface of the breast, to achieve the results as previously defined. The object of the invention is to place pressure upon the breast, similar to that as applied by the tongue of the infant, when naturally feeding of mother's milk. And, as known, the pump means itself associated with this particular invention may likewise be strapped to the body of the mother, to make it more convenient during usage, and the pump may be either hard-wired for connection to an electrical source, or have a battery means operatively associated therewith, to make the breast pump energy operated. It may be attached to a manual breast pump, also. This assures the portability of the breast pump, and its shield, and its sealing ring, when all integrated together during usage, may be more convenient for the new mother, to use the same for collection purposes.

It is, therefore, the principal object of this invention to provide a physiological stimulator, that is applied to the shield of a breast pump, and then applied to the breast of the mother, in order to enhance the efficiency and maximize the quantity of breast milk being collected, from the new mother.

A further object of this invention is to provide a further positive pressure to the breast that simulates the positive pressure exerted by the infant, by exerting a tongue force upon a segment of the breast, in order to induce and enhance the flow of mother's milk, for collection.

A further object of this invention is to provide the combination of a breast pump shield, with its sealing ring, and having a stimulator means that induces greater flow of mother's milk from the breast, during usage.

Another object of this invention is to maximize sealing of the pump to the breast, with all of the associated advantages.

Another object of this invention is to provide means for simulating the application of the infant's tongue to the breast during a milk collecting cycle.

Another object of this invention is the utilization of a port upon the shield that conveniently connects to the tubing from the breast pump for ease of collecting of the mother's milk during processing.

A further object of this invention is to physiologically emulate an infant sucking frequency, and the physical patterns and pressure amounts applied by the infant's tongue during a feeding cycle.

These and other objects may become more apparent to those skilled in the art upon review of the summary of the invention as provided herein, and upon undertaking a study of the description of its preferred embodiment, in view of the drawings.

DESCRIPTION OF THE PREFERRED EMBODIMENT

Figure 1:
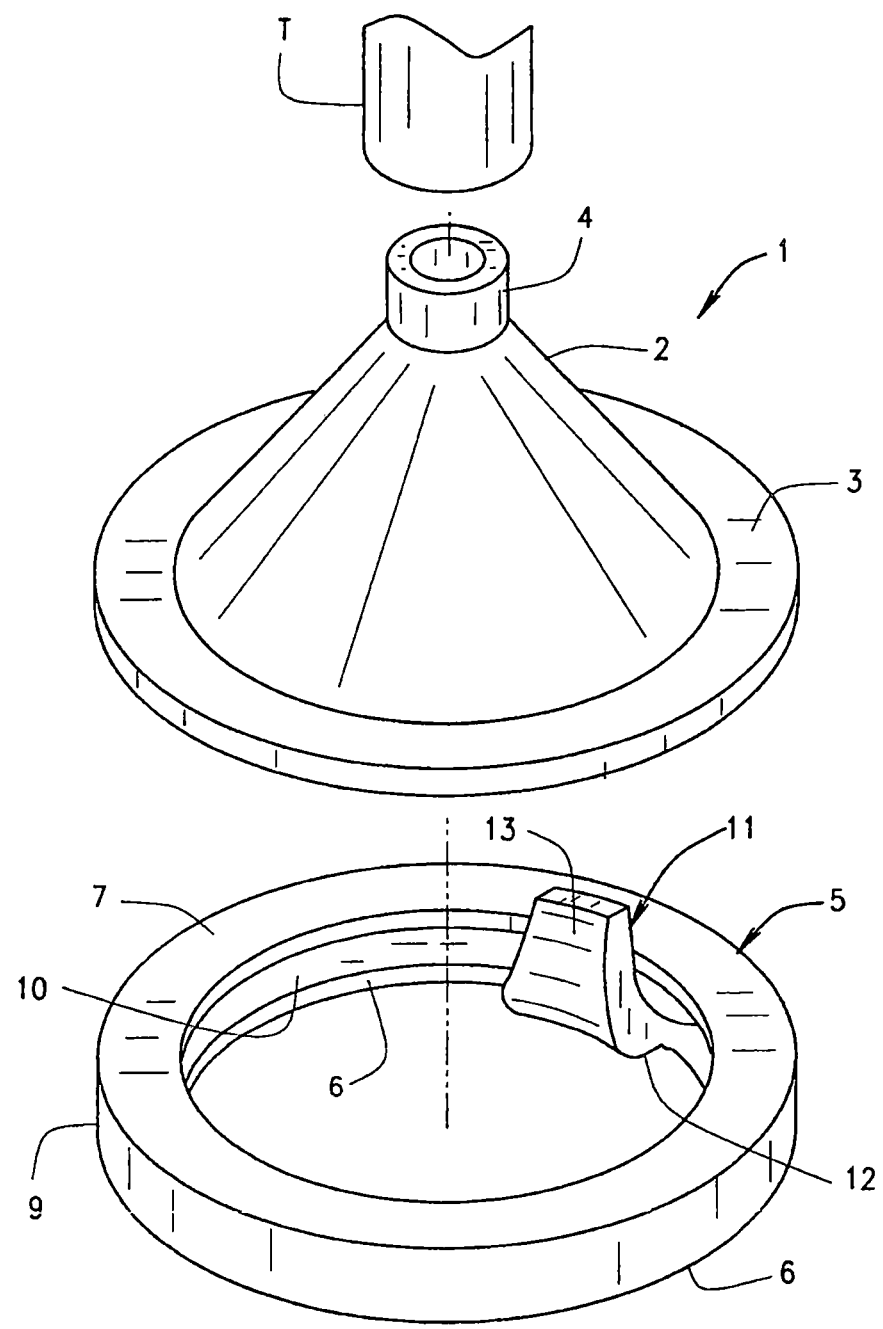
FIG. 1 is an exploded view of the physiological stimulator integral of shield for breast pump.

In referring to the drawings, and in particular FIG. 1, therein is shown the combination of the breast shield 1 generally formed with a conical section 2 and having an integral flange 3 at its bottom, and a funnel like portion 4 at its upper end, which accommodates the fastening of the tubing from the breast pump, as at tube T, thereon, during preparation for usage of the device. Shown separately, downwardly therefrom, is the sealing ring 5 and which includes a C-section like interior channel or annulus 10, having an integral upper flange 7 and an integral lower flange 6 and which are secured together by means of a base member 9 with the interior channel or annulus 10 and the ring facing inwardly, about the annulus forming the ring 5.

Connecting to the lower flange 6 is the physiological stimulator 11 of the invention. It connects with or is integrally formed extending inwardly from the inner lower edge of the ring 5, as at 12, and then further extends inwardly and upwardly as at an upwardly extending portion 13 so that when the flange 3 of the shield locates within the interior channel or annulus 10 of the C-shaped interior channel or annulus 10, the stimulator rests against the interior surface, as at 14, of the shield, extending approximately halfway up the interior of the shield, and for the following purposes.

Essentially, the stimulator 11 is designed to emulate the action of the tongue of the infant, as it impresses upon the surface of the mother's breast, and to help stimulate the discharge of the mother's milk, during a feeding cycle. But, obviously, during the usage of a breast pump, there is no infant tongue available for that purpose. Hence, the stimulator 11, and in particular its upwardly extending portion 13, resting against the interior of the shield 1, is designed to press upon the surface of the breast, and to act as a stimulator for inducing the discharge of the mother's milk, even during the application of a breast pump, for mother's milk collection purposes. Optimally, the proximal aspect of the physiological stimulator is thicker than the distal aspect, to provide the automatic and physiological peristaltic action during the negative pressure application, without using any extra parts. Hence, and what is more unique about the usage of this artificial type of stimulator, is that the ring, or the shield, can be pivoted, even approximately 360 degrees in its location, to act as a stimulator upon all surfaces of the breast, during usage of this development, in combination with the breast pump, to induce the flow of mother's milk, for collection. It is already known in the art that these breast pumps are readily available for usage, and the pump that is attached into the shield, and through the tube T by the breast pump, is usually transferred to a bag, for collection, and for later usage and application in the feeding of the infant.

The shield, its ring, and its stimulator 11, may be made of any soft type of polymer, such as an acrylic resin, for transparent purposes, and of a silicone polymer, which is a polymerized organic siloxanes, which has a soft texture, and therefore, its ring can properly seal against the body of the mother, in order to make the breast pump operate more efficiently and effectively, and furthermore, its stimulator 11 has a soft texture, so that it can feel more like the tongue of the infant, and not be abrasive or cause any inflammation to the breast, during prolonged usage.

Figure 2:
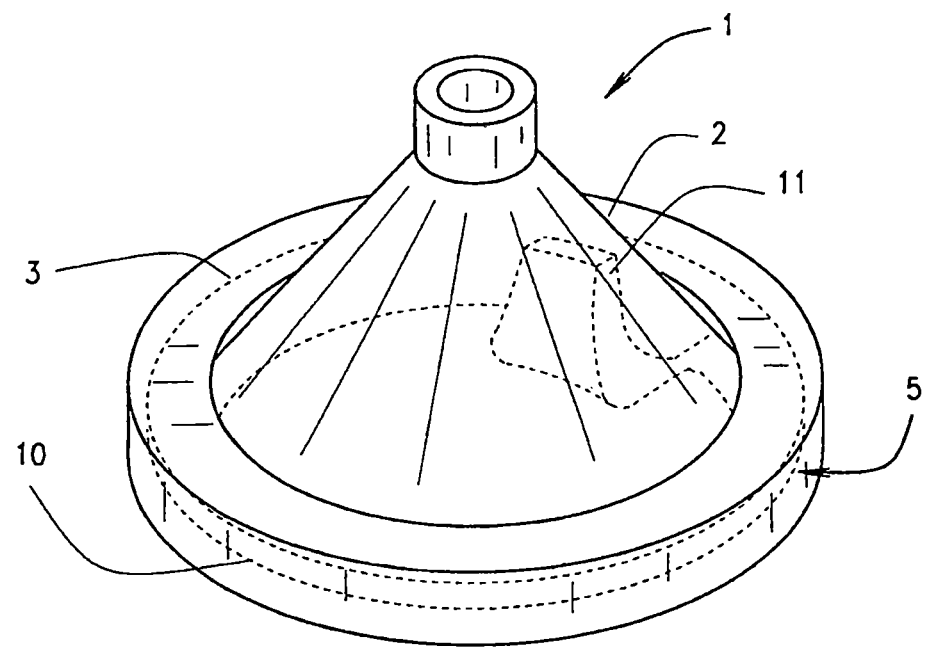
FIG. 2 is an isometric view of the combined ring with said shield, and showing the applied stimulator.

FIG. 2 shows the combination of the shield 1, with its applied ring 5 wherein the flange 3 of the shield fits within the interior channel or annulus 10 of the ring, when the two are combined together in preparation for usage. And, it shows the application of the stimulator 11 resting in proximity or continuously with the inner surface of the conical section 2 of the shield, in preparation for its usage, and in the location where it will press against the breast of the mother, during application of the breast pump.

Figure 3:
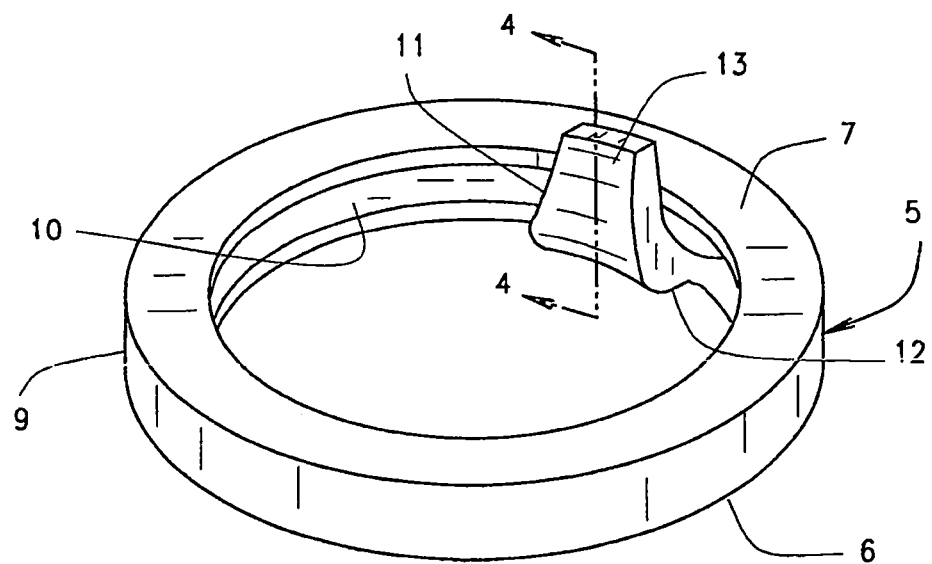
FIG. 3 is an isometric view of the ring of the shield showing the physiological stimulator integral therewith.

FIG. 3 shows just the ring 5, its upper flange 7, its lower flange 6 and its outer base member 9, all integrally formed together, and its interior channel or annulus 10 that cooperates for holding the flange 3 of the shield into position, during usage. Obviously, for cleaning purposes, the shield 1 can be easily extracted from the interior of the flexible ring 5, after completion of a breast pump cycle of usage. In addition, the stimulator 11 can be seen, extending integrally from the lower flange 6, as at 12, and then extending upwardly, as at an upwardly extending portion 13, to function for the purposes of stimulating the production of the mother's milk, during usage of the breast pump.

The physiological stimulator 11 does extend up some distance within the associated shield, approximately halfway up the interior of the associated shield, more or less, when installed with the ring for connection to the breast pump. Furthermore, the width of the stimulator, in order to simulate the infant's tongue, may extend for approximately some degrees, along the sector of the circumference of the sealing ring, perhaps in the vicinity of 2-20 degrees, more or less, in width. In the extension of the stimulator within the shield, it has been found that an extension of approximately ½-1½ inches in length, have worked satisfactorily. Furthermore, the width of the stimulator may be wider, where it connects with the lower flange of the sealing ring, than at its upper extension, that locates within the shield of the pump. As an alternative, it is possible that the stimulator could be molded upon the inner surface of the shield, approximately at the location as can be seen in FIG. 2, and therein acts as a means for enhancing the flow of mother's milk, during usage.

Figure 4:
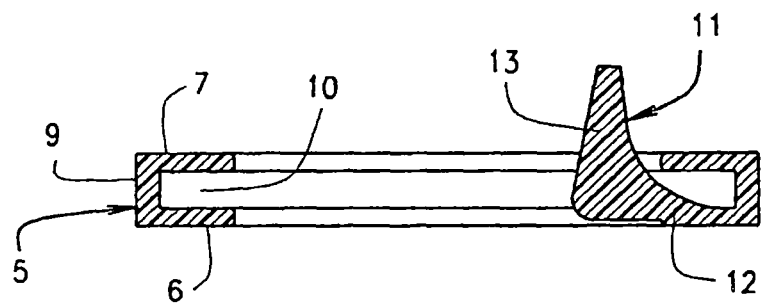
FIG. 4 is a sectional view taken along the line 4-4 of FIG. 3.

FIG. 4 provides a clearer sectional view of the ring 5, its various components such as the upper flange 7, the lower flange 6, and the base member 9 integrally formed between the two. And, the inner channel or annulus 10 that accommodates the location of the shield flange 3, can be seen. More specifically, the stimulator 11 as integrally formed with the lower flange 6, as at that juncture 12, is clearly noted. And, the upward portion of the stimulator, as at an upwardly extending portion 13, that extends upwardly and locates contiguously with the inner surface of the shield 1, can now be quite clearly seen.

Figure 5:
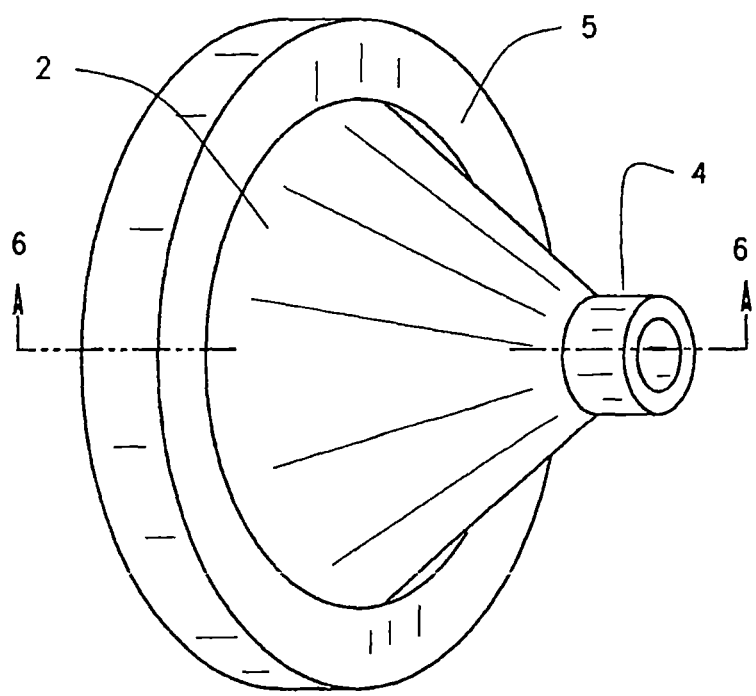
FIG. 5 is an isometric view of the combined ring and shield.

FIG. 5 shows an isometric view of the combined shield 1 and its associated ring 5. Also, can be seen is the upper portion of the shield, as the port 4, integral of the said shield, that connects with the tubing of the breast pump.

Figure 6:
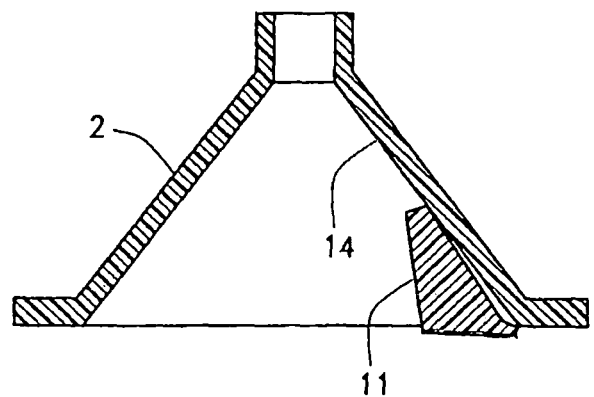
FIG. 6 is a sectional view of the shield, taken along the line 6-6 of FIG. 5.

FIG. 6 discloses a cross-section of the shield 1, and how the stimulator 11 rests against the interior of the shield, during application when extracting breast milk from the mother. Actually, this stimulator may be formed upon the inner surface of the shield to function for the purposes of this invention.

Figure 7:
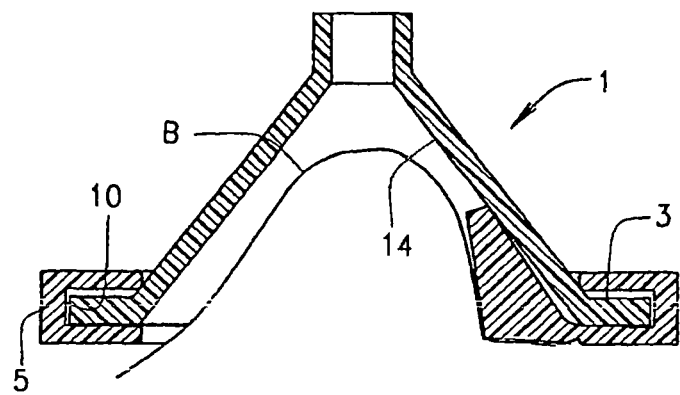
FIG. 7 is a schematic sectional view of the shield and ring with integral stimulator as applied during usage.

FIG. 7 provides an overall schematic view of the entire structure, including the existing pump shield 1, the application of its lower integral flange 3 within the inner channel or annulus 10 of the ring 5, and how it is placed upon the mother's breast B during its application.

Thus, it is believed that one can now fully understand and comprehend the structure of this particular shield, and its associated ring with the physiological stimulator formed thereon, in order to function as a means for enhancing the delivery and flow of breast milk from the mother, during its usage and application.

Variations or modifications to the subject matter of this invention may occur to those skilled in the art upon the study of the invention as described herein. Any variations upon the structure of the overall concept of this invention, as described in the summary of the invention, explained in detail in the description of the preferred embodiment, in view of the drawings, are meant to be encompassed within the scope of any claims to patent protection issuing upon this invention. The depiction of the invention as set forth in the drawings are primarily set forth for illustrative purposes.

I claim:

1. A physiological stimulator and a shield component for a breast pump, comprising a sealing ring, said sealing ring being shaped to accommodate insertion of the shield component therein, with said sealing ring having an integral annulus opening directed inwardly of said sealing ring, said shield component having a conical segment which at a lower end of said conical segment includes a slightly flaring flange, said slightly flaring flange is provided for fitting into the sealing ring when preparing said shield component for usage with the breast pump;

said physiological stimulator is integrally formed with an interior of the sealing ring, said stimulator extending radially inward from an interior of the shield component and having an upwardly extending portion extending upwardly into the interior of the shield component, the upwardly extending portion being non-annular, but arcuate, and spaced from and located within the shield component, and the stimulator therein is configured to be biased against a breast of a lactating mother to enhance and induce delivery of milk during usage of said shield component with the breast pump during operation of the breast pump, wherein the stimulator, during operation of the breast pump, moves with peristaltic action driven by negative pressure of the breast pump;

wherein a proximal aspect of the stimulator that is configured to contact a body of the lactating mother is thicker than a distal aspect of the stimulator configured to extend away from the body of the lactating mother.

2. The physiological stimulator and the shield component of claim 1, wherein said stimulator and said shield component are formed of a polymer.

3. The physiological stimulator and the shield component of claim 2, wherein said polymer comprises acrylic resin.

4. The physiological stimulator and the shield component of claim 2, wherein said polymer comprises silicone.

5. The physiological stimulator and the shield component of claim 1, wherein the stimulator comprises a first end that connects with a lower flange of the sealing ring and a second end at a terminus of the stimulator that extends upwardly within the interior of the shield component, such that said first end is wider than said second end.

* * * * *